United States Patent
Arnold et al.

(10) Patent No.: US 6,500,865 B1
(45) Date of Patent: Dec. 31, 2002

(54) SULFONAMIDE DERIVATIVES

(75) Inventors: Macklin Brian Arnold, Morgantown, IN (US); Thomas John Bleisch, Noblesville, IN (US); Paul Leslie Ornstein, Carmel, IN (US); Edward C. R. Smith, Fishers, IN (US); Hamideh Zarrinmayeh, Carmel, IN (US); Dennis Michael Zimmerman, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/744,413

(22) PCT Filed: Jul. 28, 1999

(86) PCT No.: PCT/US99/17018

§ 371 (c)(1), (2), (4) Date: Jan. 23, 2001

(87) PCT Pub. No.: WO00/06083

PCT Pub. Date: Feb. 10, 2000

Related U.S. Application Data

(60) Provisional application No. 60/094,970, filed on Jul. 31, 1998.

(51) Int. Cl.$^7$ ................................................ A61K 31/18
(52) U.S. Cl. ..................... 514/605; 514/357; 514/438; 514/461; 514/602; 514/603; 514/604
(58) Field of Search .............................. 564/82, 95, 96, 564/97; 514/602, 603, 604, 605, 438, 357, 461; 549/76, 77

(56) References Cited

U.S. PATENT DOCUMENTS

| 4,401,663 | A  | * | 8/1983  | Buckwalter et al. |
| 6,174,922 | B1 |   | 1/2001  | Arnold et al. |
| 6,303,816 | B1 |   | 10/2001 | Arnold et al. |

FOREIGN PATENT DOCUMENTS

| DE | 197 40 785 | | 8/1998 |
| JP | 56-26865 | * | 3/1981 |
| WO | WO 99/02502 | | 7/1997 |

OTHER PUBLICATIONS

U.S. patent application Ser. No. 09/355,605, Arnold et al., filed Feb. 4, 1997.
U.S. patent application Ser. No. 09/744,457, Escribano et al., filed Jul. 31, 1998.
U.S. patent application Ser. No. 09/744,414, Arnold et al., filed Jul. 31, 1998.
U.S. patent application Ser. No. 09/744,418, Arnold et al., Jul. 31, 1998.
U.S. patent application Ser. No. 09/744,419, Arnold et al., Jul. 31, 1998.
U.S. patent application Ser. No. 09/744,460, Cantrell et al., Jul. 31, 1998.

* cited by examiner

*Primary Examiner*—Shailendra Kumar
(74) *Attorney, Agent, or Firm*—Nelsen L. Lentz

(57) ABSTRACT

The present invention provides certain sulfonamide derivatives useful for potentiating glutamate receptor function in a mammal and therefore, useful for treating a wide variety of conditions, such as psychiatric and neurological disorders.

3 Claims, No Drawings

SULFONAMIDE DERIVATIVES

This is a 371 of PCT/US99/17018 filed Jul. 28, 1999 which claims priority to U.S. Provisional Application No. 60/094,970 filed Jul. 31, 1998.

The present invention relates to the potentiation of glutamate receptor function using certain sulfonamide derivatives. It also relates to novel sulfonamide derivatives, to processes for their preparation and to pharmaceutical compositions containing them.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EM). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1959); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

AMPA receptors are assembled from four protein sub-units known as GluR1 to GluR4, while kainic acid receptors are assembled from the sub-units GluR5 to GluR7, and KA-1 and KA-2. Wong and Mayer, *Molecular Pharmacology* 44: 505–510, 1993. It is not yet known how these sub-units are combined in the natural state. However, the structures of certain human variants of each sub-unit have been elucidated, and cell lines expressing individual sub-unit variants have been cloned and incorporated into test systems designed to identify compounds which bind to or interact with them, and hence which may modulate their function. Thus, European patent application, publication number EP-A2-0574257 discloses the human sub-unit variants GluR1B, GluR2B, GluR3A and GluR3B. European patent application, publication number EP-A1-0583917 discloses the human sub-unit variant GluR4B.

One distinctive property of AMPA and kainic acid receptors is their rapid deactivation and desensitization to glutamate. Yamada and Tang, *The Journal of Neuroscience*, September 1993, 13(9): 3904–3915 and Kathryn M. Partin, *J. Neuroscience*, Nov. 1, 1996, 16(21): 6634–6647. The physiological implications of rapid desensitization, and deactivation if any, are unknown.

It is known that the rapid desensitization and deactivation of AMPA and/or kainic acid receptors to glutamate may be inhibited using certain compounds. This action of these compounds is often referred to in the alternative as "potentiation" of the receptors. One such compound, which selectively potentiates AMPA receptor function, is cyclothiazide. Partin et al., *Neuron*. Vol. 11, 1069–1082, 1993. Compounds which potentiate AMPA receptors, like cyclothiazide, are often referred to as ampakines.

International Patent Application Publication Number WO 9625926 discloses a group of phenylthioalkylsulfonamides, S-oxides and homologs which are said to potentiate membrane currents induced by kainic acid and AMPA.

U.S. Pat. No. 3,143,549 discloses certain phenylalkylsulfamides, including 1-methyl-2-phenylethyl dimethylsulfamide. The compounds are said to have central nervous system activity, in particular anti-anxiety and tranquilizing properties.

U.S. Pat. No. 3,267,139 discloses certain N'-trimethylacetyl-N-phenylalkylsulfamides and -phenylcyclopropylsulfamides having central nervous system activity and anticonvulsant activity. The compounds are also said to produce Parkinson-like symptoms in experimental animals.

U.S. Pat. No. 3,860,723 discloses a method of increasing feed intake of healthy animals using certain phenylalkylsulfamides.

Foye et al., *J. Pharm. Sci.* (1971), 60(7), 1095-6 discloses certain phenylalkyl methylsulfonamides including N-1-methyl-2-phenylethyl methanesulfonamide, having hypotensive activity.

British Patent Specification Number 1,059,360 discloses certain phenylalkylsulfamides having activity as sedatives, narcotics and anti-convulsants, including 1-(1-methyl-2-phenylethylaminosulphonyl)piperidine.

U.S. Pat. No. 4,210,749 discloses N-1-methyl-2-phenyl-3-methoxy ethyl butane-sulfonamide.

Gualtieri et al., *J. Pharm. Sci.*, (1973), 62(5), 849-851 discloses N-1-methyl-2-phenylethyl butanesulfonamide and its evaluation as a mosquito repellent.

Foye et al., *J. Pharm. Sci.* (1979), 68(5), 591-5 discloses N-1-methyl-2-(4-chlorophenyl)ethyl methane-sulfonamide.

Foye and Sane, *J. Pharm. Sci.* (1977), 66(7), 923-6 discloses N-methanesulfonyl and N-trifluoromethanesulfonyl derivatives of amphetamines and certain 4-substituted analogs thereof, and their evaluation for central nervous system and anorexic effects.

European patent application publication no. EP-A1-0657442 discloses certain naphthyloxyacetic acid derivatives as PEG2 agonists and antagonists. N-(2,2-diphenylethyl)-methanesulfonamide is disclosed as an intermediate at page 53, line 38.

U.S. Pat. No. 3,629,332 discloses certain N-aryl- and N-heteroarylalkyl fluoroalkane sulfonamides as plant growth modifiers, including N-(alpha-methylphenylethyl) trifluoromethanesulfonamide, difluoromethanesulfonamide and fluoromethanesulfonamide. Some of the compounds are also said to have other biological activity, including insecticidal, acaricidal, nematicidal, analgesic and anti-inflammatory activity.

Ampakines have been shown to improve memory in a variety of animal tests. Staubli et al., *Proc. Natl. Acad. Sci.*, Vol. 91, pp 777–781, 1994, *Neurobiology*, and Arai et al., *The Journal of Pharmacology and Experimental Therapeutics*, 278: 627–638, 1996.

It has now been found that cyclothiazide and certain sulfonamide derivatives potentiate agonist-induced excitability of human GluR4B receptor expressed in HEK 293 cells. Since cyclothiazide is known to potentiate glutamate receptor function in vivo, it is believed that this finding portends that the sulfonamide derivatives will also potentiate glutamate receptor function in vivo, and hence that the compounds will exhibit ampakine-like behavior.

The present invention provides compounds of formula I:

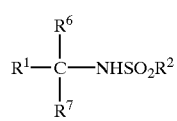

formula I wherein
$R^1$ represents a naphthyl group or a phenyl, furyl, thienyl or pyridyl group which is unsubstituted or substituted by one or two substituents selected independently from halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo(3–8C)cycloalkyl; halo (1–10C)alkyl; $(CH_2)_y X^1 R^9$ in which y is 0 or an integer of from 1 to 4, $X^1$ represents O, S, $NR^{10}$, CO, COO, OCO, $CONR^{11}$, $NR^{12}CO$, $NR^{12}COCOO$ or $OCONR^{13}$, $R^9$ represents hydrogen, (1–10C)alkyl, (3–10C) alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; pyridyl; pyridazinyl; pyrimidinyl; dihydro-thienyl; dihydrofuryl; dihydrothiopyranyl; dihydropyranyl; dihydrothiazolyl; (1–4C) alkoxycarbonyidihydrothiazolyl; (1–4C) alkoxycarbonyidimethyldihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}-(L^a)_n-X^2-(L^b)_m$ in which $X^2$ represents a bond, O, NH, S, SO, $SO_2$, CO, CH(OH), CONH, NHCO, NHCONH, NHCOO, COCONH, $OCH_2CONH$ or CH=CH, $L_a$ and $L_b$ each represent (1–4C)alkylene, one of n and m is 0 or 1 and the other is 0, and $R^{14}$ represents a phenyl or heteroaromatic group which is unsubstituted or substituted by one or two of halogen, nitro, cyano, hydroxyimino, (1–10C) alkyl, (2–10C)alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_z X^3 R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, halo(1–10C)alkyl, (1–4C)alkoxycarbonyl(1–4C)alkyl, (1–4C) alkylsulfonylamino(1–4C)alkyl, (N-(1–4C) alkoxycarbonyl)(1–4C)alkylsulfonylamino-(1–4C) alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(–4C)alkyl, di(1–4C) alkylamino and (1–4C)alkoxy and $R^{16}$, $R^{17}$, $R^{18}$ and $R^{19}$ each independently represents hydrogen or (–4C) alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group;

$R^2$ represents (1–6C)alkyl, (3–6C)cycloalkyl, fluoro (1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C) alkoxy, or a group of formula $R^3R^4N$ in which $R^3$ and $R^4$ each independently represents (1–4C)alkyl or, together with the nitrogen atom to which they are attached form an azetidinyl, pyrrolidinyl, piperidinyl, morpholino, piperazinyl, hexahydroazepinyl or octahydroazocinyl group; and $R^6$ and $R^7$ are each independently selected from the group consisting of hydrogen, (1–6C)alkyl; aryl(1–6C)alkyl; (2–6C)alkenyl; aryl(2–6C)alkenyl and aryl; or $R^6$ and $R^7$ together with the carbon atom or carbon atoms to which they are attached form a (3–8C) carbocyclic ring; or a pharmaceutically acceptable salt thereof.

The present invention further provides a method of potentiating glutamate receptor function in a mammal requiring such treatment, which comprises administering an effective amount of a compound of formula I.

According to another aspect, the present invention provides the use of a compound of formula I, or a pharmaceutically acceptable salt thereof as defined hereinabove for the manufacture of a medicament for potentiating glutamate receptor function.

In addition, the present invention provides the use of a compound of formula I or a pharmaceutically acceptable salt thereof for potentiating glutamate receptor function.

The invention further provides a method of potentiating glutamate receptor function in a mammal requiring such treatment, which comprises administering an effective amount of a compound of formula:

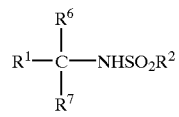

wherein
$R^1$ represents an unsubstituted or substituted aromatic or heteroaromatic group;
$R^2$ represents (1–6C)alkyl, (3–6C)cycloalkyl, fluoro (1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C) alkoxy, or a group of formula $R^3R^4N$ in which $R^3$ and $R^4$ each independently represents (1–4C)alkyl or, together with the nitrogen atom to which they are attached form an azetidinyl, pyrrolidinyl, piperidinyl, morpholino, piperazinyl, hexahydroazepinyl or octahydroazocinyl group; and $R^6$ and $R^7$ are each independently selected from the group consisting of hydrogen, (1–6C)alkyl; aryl(1–6C)alkyl; (2–6C)alkenyl; aryl(26C)alkenyl and aryl; or $R^6$ and $R^7$ together with the carbon atom or carbon atoms to which they are attached form a (3–8C) carbocyclic ring; or a pharmaceutically acceptable salt thereof.

In this specification, the term "potentiating glutamate receptor function" refers to any increased responsiveness of glutamate receptors, for example AMPA receptors, to glutamate or an agonist, and includes but is not limited to inhibition of rapid desensitization or deactivation of AMPA receptors to glutamate.

A wide variety of conditions may be treated or prevented by the compounds of formula I and their pharmaceutically acceptable salts through their action as potentiators of glutamate receptor function. Such conditions include those associated with glutamate hypofunction, such as psychiatric and neurological disorders, for example cognitive disorders; neuro-degenerative disorders such as Alzheimer's disease; age-related dementias; age-induced memory impairment; movement disorders such as tardive dyskinesia, Hungtinton's chorea, myoclonus and Parkinson's disease; reversal of drug-induced states (such as cocaine, amphetamines, alcohol-induced states); depression; attention deficit disorder; attention deficit hyperactivity disorder; psychosis; cognitive deficits associated with psychosis; and drug-induced psychosis. The compounds of formula I may also be useful for improving memory (both short term and long term) and learning ability. The present invention provides the use of compounds of formula I for the treatment of each of these conditions.

The term "treating" (or "treat") as used herein includes its generally accepted meaning which encompasses prohibiting, preventing, restraining, and slowing, stopping, or reversing progression, severity, or a resultant symptom.

The present invention includes the pharmaceutically acceptable salts of the compounds defined by formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, g-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formula I can be resolved by one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

As used herein, the term "aromatic group" means the same as aryl, and includes phenyl and a polycyclic aromatic carbocyclic ring such as naphthyl.

The term "heteroaromatic group" includes an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or another 5–6 membered ring containing one to four atoms selected from oxygen, sulfur and nitrogen. Examples of heteroaromatic groups are thienyl, furyl, oxazolyl, isoxazolyl, oxadiazoyl, pyrazolyl, thiazolyl, thiadiazolyl, isothiazolyl, imidazolyl, triazolyl, tetrazolyl, pyridyl, pyridazinyl, pyrimidyl, benzofuryl, benzothienyl, benzimidazolyl, benzoxazolyl, benzothiazolyl, indolyl and quinolyl.

The term "substituted" as used in the term "substituted aromatic or heteroaromatic group" herein signifies that one or more (for example one or two) substituents may be present, said substituents being selected from atoms and groups which, when present in the compound of formula I, do not prevent the compound of formula I from functioning as a potentiator of glutamate receptor function.

Examples of substituents which may be present in a substituted aromatic or heteroaromatic group include halogen; nitro; cyano; hydroxyimino; (1–10C) alkyl; (2–10C) alkenyl; (2–10C)alkynyl; (3–8C)cycloalkyl; hydroxy(3–8C) cycloalkyl; oxo(3–8C)cycloalkyl; halo(1–10C)alkyl; $(CH_2)_y X^1 R^9$ in which y is 0 or an integer of from 1 to 4, $X^1$ represents O, S, $NR^{10}$, CO, COO, OCO, $CONR^{11}$, $NR^{12}CO$, $NR^{12}COCOO$, $OCONR^{13}$, $R^9$ represents hydrogen, (1–10C) alkyl, (3–10C)alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; pyridyl; pyridazinyl; pyrimidinyl; dihydrothienyl; dihydrofuryl; dihydrothiopyranyl; dihydropyranyl; dihydrothiazolyl; (1–4C)alkoxycarbonyl dihydrothiazolyl; (1 4C)alkoxycarbonyl dimethyl-dihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$, or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen; nitro; cyano; (1–10C) alkyl; (2–10C)alkenyl; (2–10C)alkynyl; (3–8C)cycloalkyl; 4-(1,1-dioxotetrahydro-1,2-thiazinyl); halo(1–10C)alkyl; cyano(2–10C)alkenyl; phenyl; and $(CH_2)_z X^3 R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, $OCONR^{19}$ or $NR^{19}COO$, $R^{15}$ represents hydrogen, (1–10C) alkyl, phenyl(1–4C)alkyl, halo (1–10C)alkyl, (1–4C) alkoxycarbonyl(1–4C)alkyl, (1–4C)alkylsulfonylamino (1–4C)alkyl, N-(I4C)alkoxycarbonyl)(1–4C) alkylsulfonylamino(1–4C)alkyl, (3–10C)alkenyl, (3–1oC) alkynyl, (3–8C)cycloalkyl, camphoryl, or an aromatic or heteroaromatic group which is unsubstituted or substituted by one or two of halogen, (1–4C)alkyl, halo(1–4C)alkyl, di(1–4C)alkylamino and (1–4C)alkoxy, and $R^{16}$, $R^{17}$, $R^{18}$ and $R^{19}$ each independently represents hydrogen or (1–10C) alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group.

The term (1–10C)alkyl includes (1–8C)alkyl, (1–6C)alkyl and (1–4C)alkyl. Particular values are methyl, ethyl, propyl, isopropyl, butyl, isobutyl, t-butyl, pentyl, hexyl, heptyl, octyl, nonyl and decyl.

The term (2–10C)alkenyl includes (3–10C)alkenyl, (1–8C)alkenyl, (1–6C)alkenyl and (1–4C)alkenyl. Particular values are vinyl and prop-2-enyl.

The term (2–10C)alkynyl includes (3–10C)alkynyl, (1–8C)alkynyl, (1–6C)alkynyl and (3–4C)alkynyl. A particular value is prop-2-ynyl.

The term (3–8C)cycloalkyl, as such or in the term (3–8C) cycloalkyloxy, includes monocyclic and polycyclic groups. Particular values are cyclopropyl, cyclobutyl, cyclopentyl, cyclohexyl and bicyclo[2.2.2]octane. The term includes (3–6C)cycloalkyl: cyclopropyl, cyclobutyl, cyclopentyl and cyclohexyl.

The term hydroxy(3–8C)cycloalkyl includes hydroxycyclopentyl, such as 3-hydroxycyclopentyl.

The term oxo(3–8C)cycloalkyl includes oxocyclopentyl, such as 3-oxocyclopentyl.

The term halogen includes fluorine, chlorine, bromine and iodine.

The term halo(1–10C)alkyl includes fluoro(1–10C)alkyl, such as trifluoromethyl and 2,2,2-trifluoroethyl, and chloro (1–10C)alkyl such as chloromethyl.

The term cyano(2–10C)alkenyl includes 2-cyanoethenyl.

The term (2–4C)alkylene includes ethylene, propylene and butylene. A preferred value is ethylene.

The term thienyl includes thien-2-yl and thien-3-yl.

The term furyl includes fur-2-yl and fur-3-yl.

The term oxazolyl includes oxazol-2-yl, oxazol4-yl and oxazol-5-yl.

The term isoxazolyl includes isoxazol-3-yl, isoxazol4-yl and isoxazol-5-yl.

The term oxadiazolyl includes [1,2,4]oxadiazol-3-yl and [1,2,4]oxadiazol-5-yl.

The term pyrazolyl includes pyrazol-3-yl, pyrazol4-yl and pyrazol-5-yl.

The term thiazolyl includes thiazol-2-yl, thiazol-4-yl and thiazol-5-yl.

The term thiadiazolyl includes [1,2,4]thiadiazol-3-yl, and [1,2,4]thiadiazol-5-yl.

The term isothiazolyl includes isothiazol-3-yl, isothiazol4-yl and isothiazol-5-yl.

The term imidazolyl includes imidazol-2-yl, imidazolyl4-yl and imidazolyl-5-yl.

The term triazolyl includes [1,2,4]triazol-3-yl and [1,2,4]triazol-5-yl.

The term tetrazolyl includes tetrazol-5-yl.

The term pyridyl includes pyrid-2-yl, pyrid-3-yl and pyrid4-yl.

The term pyridazinyl includes pyridazin-3-yl, pyridazin4-yl, pyridazin-5-yl and pyridazin6-yl.

The term pyrimidyl includes pyrimidin-2-yl, pyrimidin4-yl, pyrimidin-5-yl and pyrimidin6-yl.

The term benzofuryl includes benzofur-2-yl and benzofur-3-yl.

The term benzothienyl includes benzothien-2-yl and benzothien-3-yl.

The term benzimidazolyl includes benzimidazol-2-yl.

The term benzoxazolyl includes benzoxazol-2-yl.

The term benzothxazolyl includes benzothiazol-2-yl.

The term indolyl includes indol-2-yl and indol-3-yl.

The term quinolyl includes quinol-2-yl.

The term dihydrothiazolyl includes 4,5-dihydrothiazol-2-yl, and the term (1–4C)alkoxycarbonyldihydrothiazolyl includes 4-methoxycarbonyl4,5-dihydrothiazol-2-yl.

Preferably each of $R^6$ and $R^7$ independently represent (16C)alkyl, aryl(1–6C)alkyl, (2–6C)alkenyl, aryl(2–6C)alkenyl or aryl, or $R^6$ and $R^7$ together with the carbon atom or carbon atoms to which they are attached form a (3–8C) carbocyclic ring.

Examples of a (1–6C)alkyl group represented by $R^6$ and $R^7$ are methyl, ethyl and propyl. An example of an aryl(1-C)alkyl group is benzyl. An example of a (2–6C)alkenyl group is prop-2-enyl. An example of a (3–8C)carbocyclic ring is a cyclopropyl ring.

More preferably, $R^6$ and $R^7$ each independently represent hydrogen or (1–4C)alkyl, or together with the carbon atom to which they are attached form a (3–8C) carbocyclic ring.

More preferably $R^6$ and $R^7$ each independently represent hydrogen, methyl or ethyl, or $R^6$ and $R^7$ together with the carbon atom to which they are attached form a cyclopropyl ring.

Preferably $R^3$ and $R^4$ each represent methyl.

Examples of values for $R^2$ are methyl, ethyl, propyl, 2-propyl, butyl, 2-methylpropyl, cyclohexyl, trifluoromethyl, 2,2,2-trifluoroethyl, chloromethyl, ethenyl, prop-2enyl, methoxyethyl, phenyl, 4-fluorophenyl, or dimethylamino. Preferably $R^2$ is ethyl, 2-propyl or dimethylamino.

Examples of values for $R^9$ are hydrogen, methyl, ethyl, propyl, isopropyl, t-butyl, ethenyl, cyclopropyl, cyclobutyl, cyclopentyl, cyclohexyl, 2-pyrrolidinyl, morpholino or 2-tetrahydrofuryl.

Examples of values for $R^{15}$ are hydrogen, methyl, ethyl, propyl, isopropyl, butyl, t-butyl, benzyl, 2,2,2-trifluoroethyl, 2-methoxycarbonylethyl, cyclohexyl, 10-camphoryl, phenyl, 2-fluorophenyl, 3-fluorophenyl, 2-trifluoromethylphenyl, 4-trifluoromethylphenyl, 2-methoxyphenyl, 3-methoxyphenyl, 4-methoxyphenyl, 1-(5-dimethylamino)naphthyl, and 2thienyl.

$X^1$ preferably represents O, CO, CONH or NHCO.

z is preferably 0.

$R^9$ is preferably (1–4C)alkyl, (2–4C)alkenyl, (3–6C)cycloalkyl, pyrrolidinyl, morpholino or tetrahydrofuryl.

Particular values for the groups $(CH_2)_yX^1R^9$ and $(CH_2)_zX^3R^{15}$ include (1–10C)alkoxy, including (1–6C)alkoxy and (1–4C)alkoxy, such as methoxy, ethoxy, propoxy, isopropoxy and isobutoxy; (3–10C)alkenyloxy, including (3–6C)alkenyloxy, such as prop-2-enyloxy; (3–10C)alkynyloxy, including (3–6C)alkynyloxy, such as prop-2-ynyloxy; and (1–6C)alkanoyl, such as formyl and ethanoyl.

Examples of particular values for y are 0 and 1.

Examples of particular values for z are 0, 1, 2 and 3.

$L^a$ and $L^b$ preferably each independently represents $CH_2$.

$X^2$ preferably represents a bond, O, NH, CO, CH(OH), CONH, NHCONH or $OCH_2CONH$.

Preferably the group $(CH_2)_yX^1R^9$ represents CHO; $COCH_3$, $OCH_3$; $OCH(CH_3)_2$; $NHCOR^9$ in which $R^9$ represents methyl, ethyl, isopropyl, t-butyl, ethenyl, cyclopropyl, cyclobutyl, cyclopentyl, cyclohexyl, 2-pyrolidinyl or morpholino; $CONHR^9$ in which $R^9$ represents cyclopropyl or cyclopentyl; NHCOCOOCH3; or 2-tetrahydrofurylmethoxy.

Preferably the group $(CH_2)_zX^3R^{15}$ represents $NH_2$; $CH_2NH_2$; $(CH_2)_2NH_2$; $(CH_2)_3NH_2$; $CONH_2$; $CONHCH_3$; $CON(CH_3)_2$; $N(C_2H_5)_2$; $CH_2OH$; $CH(OH)CH_3$; $CH(OH)CH_2CH_3$; CHO; $COCH_3$; COOH; $COOCH_3$; $CH_2NHCOOC(CH_3)_3$; $(CH_2)_2NHCOOC(CH_3)_3$; $NHSO2CH(CH_3)_2$; a group of formula $(CH_2)_2NHSO_2R^{15}$ in which $R^{15}$ represents $CH_3$, $CH_2CH_3$, $CH(CH_3)_2$, $(CH_2)_2CH_3$, $(CH_2)_3CH_3$, benzyl, $CH_2CF_3$, 2-methoxycarbonylethyl, cyclohexyl, 10-camphoryl, phenyl, 2-fluorophenyl, 4-fluorophenyl, 2-trifluoromethylphenyl, 4-trifluoromethylphenyl, 4-methoxyphenyl, 1-(2-dimethylamino)naphthyl or 2-thienyl; $CH(OH)CH_2NHSO_2CH_3$; $(CH_2)_3NHSO_2CH(CH_3)_2$; $COCH_2NOCOCCH_3)_2SO_2CH_3$; $COCH_2NHSO_2CH_3$; $(CH_2)_2NHCOR^{15}$ in which $R^{15}$ represents $CH_3$, $CH(CH_3)_2$, $CH_2CH(CH_3)_2$, phenyl, 3-fluorophenyl, 4-fluorophenyl, benzyl, 2-methoxyphenyl, 4-methoxyphenyl, 2-thienyl, CH═CH, CH═CHCN, $OCH_3$ or $O(CH_2)_3CH_3$.

Examples of particular values for $(L^a)_n$—$X^2$—$(L^b)_m$ are a bond, O, NH, S, SO, $SO_2$, CO, $CH_2$, $COCH_2$, COCONH, $CH(OH)CH_2$, CONH, NHCO, NHCONH, $CH_2O$, $OCH_2$, $OCH_2CONH$, $CH_2NH$, $NHCH_2$ and $CH_2CH_2$.

$R^{14}$ is preferably an unsubstituted or substituted phenyl, naphthyl, furyl, thienyl, isoxazolyl, thiazolyl, tetrazolyl, pyridyl, pyrimidyl benzothienyl or benzothiazolyl group.

Examples of particular values for $R^{14}$ are phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 2,3-difluoro-phenyl, 2,4-difluorophenyl, 3,4-dichlorophenyl, 3,5-dichlorophenyl, 4-cyanophenyl, 3-nitrophenyl, 4-hydroxyiminophenyl, 2-methylphenyl, 4-methylphenyl, 4-ethylphenyl, 3-propylphenyl, 4-t-butylphenyl, 2-prop-2-enylphenyl, 4-(4-(1, 1-dioxotetrahydro-1,2-thiazinyl) phenyl, 2-trifluoromethylphenyl, 3-trifluoromethylphenyl, 4-trifluoromethylphenyl, 2-bromomethylphenyl, 2-fluoro 4-trifluoromethylphenyl, 4-(2-cyanoethenyl)phenyl, 4-phenyl, 2-formylphenyl, 3-formylphenyl, 4-formylphenyl, 2-acetylphenyl, 3-acetylphenyl, 4-acetylphenyl, 2-propanoylphenyl, 2-(2-methyl-propanoyl)phenyl, 2-methoxyphenyl, 3-methoxyphenyl, 4-methoxyphenyl, 4-butoxyphenyl, 2-hydroxymethylphenyl, 4-hydroxymethylphenyl, 2-(1-hydroxyethyl)phenyl, 3-(1-hydroxyethyl)phenyl, 4-(1-hydroxyethyl)phenyl, 2-(1-hydroxypropyl)phenyl, 4-(1-hydroxypropyl)phenyl, 2-(1-hydroxy-2,2-dimethyl-propyl)phenyl, 4-trifluoromethoxyphenyl, 2-aminophenyl,4-aminophenyl, 4-N,N-diethylaminophenyl, 4-aminomethylphenyl, 4-(2-aminoethyl)phenyl, 4-(3-aminopropyl)phenyl, 4-carboxyphenyl, 4-carbamoylphenyl, 4-N-methylcarbamoylphenyl, 4-N,Ndimethylcarbamoylphenyl, 2-isopropylaminomethylphenyl, 4-t-butoxycarbonylaminomethylphenyl, 4-(2-isopropoxycarboxamido)ethylphenyl, 4-(2-butoxycarboxamido)ethylphenyl, 4-isopropylsulfonylaminophenyl, 4-(2-methanesulfonylamino)ethylphenyl, 4-(2-ethylsulfonylamino)ethylphenyl, 4-(3-isopropylsulfonylamino)propylphenyl, 4-(1-(2-(2-propane)sulfonylamino)propyl)phenyl, 4-(2-propylsulfonyl-amino)ethylphenyl, 4-(2-isopropylsulfonylamino)ethylphenyl, 4-(2-butylsulfonylamino)ethylphenyl, 4-( 1-isopropylsulfonylaminomethyl )ethylphenyl, 4-(1-hydroxy-2-methane-sulfonylamino)ethylphenyl, 4-(2-(2,2,2-trifluoroethyl)-sulfonylaminoethyl)phenyl, 4-(2-cyclohexylsulfonylamino)-ethylphenyl, 4-(2-(2,2,2-trifluoroethyi)sulfonylamino)-ethylphenyl, 4-(2-N,N-dimethylaminosulfonylamino)-ethylphenyl, 4-(2-phenylsulfonylaminoethyl)phenyl, 4-(2-(2-fluorophenyl) sulfonylaminoethyl)phenyl, 4-(2-(4-fluoro-phenyl) sulfonylaminoethyl)phenyl, 4-(2-(2-trifluoromethyl-phenyl) sulfonylaminoethyl)phenyl, 4-(2-(4-trifluoro-methylphenyl) sulfonylaminoethyl)phenyl, 4-(2-(4-methoxyphenyl) sulfonylaminoethyl)phenyl, 4-(2-(1-(5-dimethylamino) napthalenesulfonylamino)ethyl)phenyl, 4-(2-(2-thienyl) sulfonylamino)ethyl)phenyl, 4-(2-benzamidoethyl)-phenyl, 4-(2-(4-fluorobenzamido)ethyl)phenyl, 4-(2-(3-methoxybenzamido)ethyl)phenyl, 4-(2-(3-fluorobenzamido)-ethyl)phenyl, 4-(2-(4-methoxybenzamido)ethyl)phenyl, 4-(2-(2-methoxybenzamido)ethyl)phenyl, 4-(1-(2-(2-methoxycarbonylethanesulfonylamino)ethyl)phenyl, 4-(1-(2-(10-camphorsulfonylamino)ethyl)phenyl, 4-(1-(2-(benzylsulfonyl-amino)ethyl)phenyl, 4-(2-phenylacetamido)ethyl)phenyl, 4-methanesulfonylaminoethanoylphenyl, 4-(N-(t-butoxycarbonyl)methanesulfonylaminoethanoyl)phenyl, 4-(2-(2-thienylcarboxamido)ethyl)phenyl, thien-2-yl, 5-hydroxymethylthien-2-yl, 5-formylthien-2-yl, thien-3-yl, 5-hydroxymethylthien-3-yl, 5-formylthien-3-yl, 2-bromothien-3-yl, fur-2-yl, 5-nitrofur-2-yl, fur-3-yl, isoxazol-5-yl, 3-bromoisoxazol-5-yl, isoxazol-3-yl, 5-trimethylsilylisoxazol-3-yl, 5-methylisoxazol-3-yl, 5-hydroxymethylisoxazol-3-yl, 5-methyl-3-phenylisoxazol4-yl, 5-(2-hydroxyethyl)isoxazol-3-yl, 5-acetylisoxazol-3-yl, 5-carboxyisoxazol-3-yl, 5-N-methylcarbamoylisoxazol-3-yl, 5-methoxycarbonylisoxazol-3-yl, 3-bromo[1,2,4]oxadiazol-5-yl, pyrazoi-1-yl, thiazol-2-yl, 4-hydroxymethylthiazol-2-yl, 4-methoxycarbonylthiazol-2-yl, 4-carboxythiazol-2-yl, imidazol-1-yl, 2-sulfhydryl-imidazol-1-yl, [1,2,4]triazol-1-yl, tetrazol-5-yl, 2-methyltetrazol-5-yl, 2-ethyltetrazol-5-yl, 2-isopropyl-tetrazol-5-yl, 2-(2-propenyl)tetrazol-5-yl, 2-benzyl-tetrazol-5-yl, pyrid-2-yl, 5-ethoxycarbonylpyrid-2-yl, pyrid-3-yl, 6-chloropyrid-3-yl,pyrid4-yl, 5-trifluoromethylpyrid-2-yl, 6-chloropyridazin-3-yl, 6-methylpyridazin-3-yl, 6-methoxypyrazin-3-yl, pyrimidin-5-yl, benzothien-2-yl, benzothiazol-2-yl, and quinol-2-yl.

Examples of an unsubstituted or substituted aromatic or heteroaromatic group represented by $R^1$ are unsubstituted or substituted phenyl, furyl, thienyl (such as 3-thienyl) and pyridyl (such as 3-pyridyl).

More preferably, $R^1$ represents 2-naphthyl or a group of formula

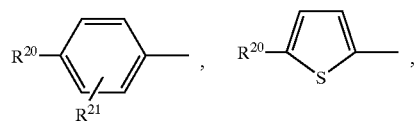

-continued

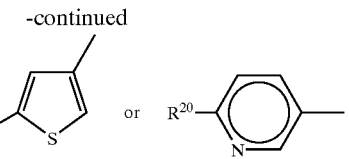

in which $R^{20}$ represents halogen; nitro; cyano; hydroxyimino; (1–10C)alkyl; (2–10C)alkenyl; (2–10C)alkynyl; (3–8C)cyclo-alkyl; hydroxy(3–8C)cycloalkyl; oxo (3–8C)cycloalkyl; halo(1–10C)alkyl; $(CH_2)_y X^1 R^9$ in which y is 0 or an integer of from 1 to 4, $X^1$ represents O, S, $NR^{10}$, CO, COO, OCO, $CONR^{11}$, $NR^{12}CO$, $NR^{12}COCOO$, $OCONR^{13}$, $R^9$ represents hydrogen, (1–10C) alkyl, (3–10C)alkenyl, (3–10C)alkynyl, pyrrolidinyl, tetrahydrofuryl, morpholino or (3–8C) cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl (1–4C) alkylpiperazinyl; thienyl; furyl; oxazolyl; isoxazolyl; pyrazolyl; imidazolyl; thiazolyl; tetrazolyl; pyridyl; pyridazinyl; pyrimidinyl; dihydrothienyl; dihydrofuryl; dihydrothiopyranyl; dihydropyranyl; dihydrothiazolyl; (1–4C) alkoxycarbonyl-dihydrothiazolyl; (1–4C) alkoxycarbonyldimethyl-dihydrothiazolyl; tetrahydrothienyl; tetrahydrofuryl; tetrahydrothiopyranyl; tetrahydropyranyl; indolyl; benzofuryl; benzothienyl; benzimidazolyl; benzothiazolyl; and a group of formula $R^{14}—(L^a)_n—X^2—(L^b)m$ in which $X^2$ represents a bond, O, NH, S, SO, $SO_2$, CO, CH(OH), CONH, NHCONH, NHCOO, COCONH, $OCH_2CONH$ or CH=CH, NHCO, $L^a$ and $L^b$ each represent (1–4C) alkylene, one of n and m is 0 or 1 and the other is 0, and $R^{14}$ represents a phenyl or hetero-aromatic group which is unsubstituted or substituted by one or two of halogen; nitro; cyano; (1–10C)alkyl; (2–10C)alkenyl; (2–10C)alkynyl; (3–8C)cycloalkyl; 4-(1,1-dioxotetrahydro-1,2-thiazinyl); halo(1–10C)alkyl; cyano(2–10C)alkenyl; phenyl; $(CH_2)_z X^3 R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2 NR^{17}$, NHCONH, $OCONR^{19}$ or $NR^{19}COO$, $R^{15}$ represents hydrogen, (1–10C)alkyl, phenyl(1–4C)alkyl, halo(1–10C)alkyl, (1–4C) alkoxycarbonyl(1–4C)alkyl, (1–4C) alkylsulfonylamino(1–4C)alkyl, (N-(1–4C) alkoxycarbonyl)(1–4C)alkylsulfonylamino(1–4C) alkyl, (3–10C)alkenyl, (3–1C)alkynyl, (3–8C) cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy, and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and $R^{21}$ represents a hydrogen atom, a halogen atom, a (1–4C)alkyl group or a (1–4C)alkoxy group.

Examples of particular values for $R^{20}$ are fluorine, chlorine, bromine, cyano, hydroxyimino, methyl, ethyl, propyl, 2-propyl, butyl, 2-methylpropyl, 1,1-dimethylethyl, cyclopentyl, cyclohexyl, 3-hydroxycyclopentyl, 3-oxocyclopentyl, methoxy, ethoxy, propoxy, 2-propoxy, acetyl, acetylamino, ethylcarboxamido, propylcarboxamido, 1-butanoylamido, t-butylcarboxamido, acryloylamido, 2-pyrrolidinylcarboxamido, 2-tetrahydrofurylmethoxy, morpholinocarboxamido, methyloxalylamido, cyclopropylcarboxamido, cyclobutylcarboxamido, cyclopentylcarboxamido, cyclohexylcarboxamido, cyclopropylcarbamoyl, cyclopentylcarbamoyl, pyrrolidin-1-yl, morpholino, piperidin-1-yl, N-methylpiperazinyl, N-benzylpiperazinyl, 2-thienyl, 3-thienyl, 2-furyl, 3-furyl, isoxazol-3-yl, thiazol-2-yl, tetrazol-5-yl, pyrid-2-yl, pyrid-3-yl, pyrid4-yl, pyrimidin-5-yl, 4,5-dihydrothiazol-2-yl, 4,5-dihydro4-methoxycarbonylthiazol-2-yl, 4,5-dihydro-4-methoxy-carbonyl-5,5-dimethylthiazol-2-yl, benzothien-2-yl, benzothiazol-2-yl, phenyl, 2-fluorophenyl, 3-fluorophenyl, 2,3-difluorophenyl, 4-chlorophenyl, 3,4-dichlorophenyl, 3,5-dichlorophenyl, 3-nitrophenyl, 4-cyanophenyl, 2-methylphenyl, 4-methylphenyl, 4-(4-(1,1-dioxotetrahydro-1,2-thiazinyl)phenyl, 3-trifluoromethylphenyl, 4-trifluoro-methylphenyl, 4-(2-cyanoethenyl)phenyl, 2-formylphenyl, 3-formylphenyl, 4-formylphenyl, 3-acetylphenyl, 4-acetylphenyl, 4-carboxyphenyl, 2-methoxyphenyl, 4-methoxyphenyl, 2-hydroxymethylphenyl, 4-hydroxymethylphenyl, 3-(1-hydroxyethyl)phenyl, 4-(1-hydroxyethyl)phenyl, 4-(1-hydroxypropyl)phenyl, 2-aminophenyl, 4-aminophenyl, 4-N,N-diethylaminophenyl, 4-aminomethylphenyl, 4-(2-aminoethyl)-phenyl, 4-(3-aminopropyl)phenyl, 4-(2-acetylaminoethyl)-phenyl, 4-t-butoxycarboxylaminoethyl) phenyl, 4-(2-t-butoxycarboxylaminoethyl)phenyl, benzylsulfonylamino, 4-isopropylsulfonylaminophenyl, 4-(2-methanesulfonyl-aminoethyl)phenyl, 4-(2-ethylsulfonylaminoethyl)phenyl, 4-(2-propylsulfonylaminoethyl)phenyl, 4-(2-butylsulfonyl-aminoethyl)phenyl, 4-(2-isopropylsulfonylaminoethyl) phenyl, 4-(2It-hydroxy-2-methanesulfonylaminoethyl) phenyl, 4-(2-dimethylaminosulfonylaminoethyl)phenyl, 4-(1-(2-(2-propyl)sulfonylaminopropyl)phenyl, 4-(2-(2,2,2-trifluoro-ethyl)sulfonylaminoethyl)phenyl, 4-(2-cyclohexylsulfonyl-aminoethyl)phenyl, 4-(2-phenylsulfonylaminoethyl)phenyl, 4-(2-(2-fluorophenyl) sulfonylaminoethyl)phenyl, 4-(2-(4-fluorophenyl) sulfonylaminoethyl)phenyl, 4-(2-(2-trifluoromethylphenyl) sulfonylaminoethyl)phenyl, 4-t2-(4-trifluoromethylphenyl) sulfonylaminoethyl)phenyl, 4-(2-(4-methoxyphenyl) sulfonylaminoethyl)phenyl, 4-(2-(1-(5-dimethylamino) napthalenesulfonylamino)ethyl)phenyl, 4-(2-(2-thienyl) sulfonylamino)ethyl)phenyl, 4-(2-benzamidoethyl)-phenyl, 4-(2-(4-fluorobenzamido)ethyl)phenyl, 4-(2-(3-methoxybenzamido)ethyl)phenyl, 4-(2-(3-fluorobenzamido)-ethyl)phenyl, 4-(2-(4-methoxybenzamido)ethyl)phenyl, 4-(2-(2-methoxybenzamido)ethyl)phenyl, 4-(2-(2-thienyl-carboxamido)ethyl)phenyl, 4-carbamoylphenyl, 4-methyl-carbamoylphenyl, 4-dimethylcarbamoylphenyl, 4-(2-(2-methylpropaneamido)ethyl)phenyl, 4-(2-(3-methyl-butaneamido)ethyl)phenyl, benzoylmethyl, benzamido, 2-fluorobenzamido, 3-flurobenzamido, 4-fluorobenzamido, 2,4-difluorobenzamido, 3-chlorobenzamido, 4-chlorobenzamido, 4-bromobenzamido, 4-iodobenzamido, 4-cyanobenzamido, 3-methylbenzamido, 4-methylbenzamido, 4-ethylbenzamido, 4-propylbenzamido, 4-t-butylbenzamido, 4-vinylbenzamido, 2-trifluoromethylbenzamido, 3-trifluoromethylbenzamido, 4-trifluoromethylbenzamido, 2-fluoro-4-trifluoromethylbenzamido, 2-methoxybenzamido, 3-methoxybenzamido, 4-methoxybenzamido, 4-butoxybenzamido, 4-phenylphenyl-carboxamido, 4-benzylcarboxamido, 4-phenoxymethyl-carboxamido, 2-fluorobenzylamino, benzyloxy, 2-fluorobenzyloxy, 2-hydroxy-2-phenylethyl, 2-fluorophenylcarbamoyl, 4-(1-(2-(2-methoxycarbonylethanesulfonylamino)ethyl)phenyl, 4-(1-(2-(10-camphorsulfonylamino)ethyl)phenyl, 4-(1-(2-(benzylsulfonylamino)ethyl)phenyl, 4-(2-phenylacetamido)-ethyl)phenyl, 4-(methanesulfonylaminoethanoyl)phenyl, 4-(N-t-butoxycarbonyl)methanesulfonylaminoethanoyl)phenyl, 2-thienylcarboxamido, 2-furylcarboxamido, 3-(5-methyl-isoxazolyl)carboxamido, 5-isoxazolylcarboxamido, 2-benzothienylcarboxamido, 4-(5-methyl-3-phenylisoxazolyl)-carboxamido, 4-pyridylcarboxamido, 2-(5-nitrofuryl)-carboxamido, 2-pyridylcarboxamido, 6-chloro-2-pyridyl-carboxamido, 2-thienylsulfonamido, 2-thienylmethylamino, 3-thienylmethylamino, 2-furylmethylamino, 3-furylmethylamino, 3-acetylureido and 2-(2-thienyl)ethylureido.

Examples of particular values for $R^{21}$ are hydrogen and chlorine. $R^{21}$ is preferably ortho to $R^{20}$.

Examples of particular values for $R^1$ are 2-naphthyl, 4-bromophenyl, 4-cyanophenyl, 4-benzamidophenyl, 4-methylphenyl, 4-isopropyl-phenyl, 4-isobutylphenyl, 4-t-butylphenyl, 4-methoxyphenyl, 4-isopropoxyphenyl, 4-cyclopentylphenyl, 4-cyclohexylphenyl, 4-(2-hydroxymethylphenyl)phenyl, 4-(4-hydroxymethylphenyl)-phenyl, 4-(2-furyl)phenyl, 4-(3-furyl)phenyl, 4-(2-thienyl)-phenyl, 4-(3-thienyl)phenyl, 4-(pyrrolidin-1-yl)phenyl, 4-(piperidin-l-yl)phenyl, 3-chloro-4-piperidin-1-ylphenyl, 4-benzyloxyphenyl, 4-(2-fluorophenyl)phenyl, 4-(3-fluoro-phenyl)phenyl, 4-(2-formylphenyl)phenyl, 4-(3-formylphenyl)-phenyl, 4-(4-formylphenyl)phenyl, 4-(4-methylphenyl)phenyl and 4-(2-methoxyphenyl)phenyl.

The compounds of formula I can be prepared as described in Scheme I below. The reagents and starting materials are readily available to one of ordinary skill in the art. All the substituents, unless otherwise specified are previously defined.

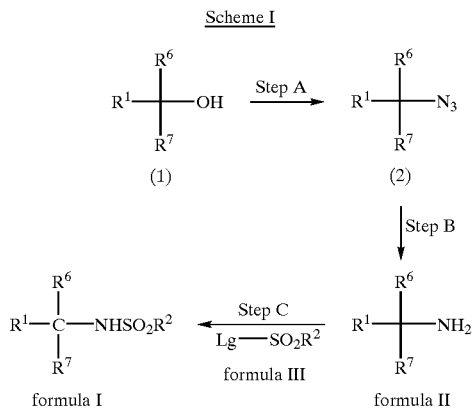

Scheme I

In Scheme I, step A, the compound of structure (1) is converted to the azido compound of structure (2) under conditions well known in the art. For example, the compound (1) is dissolved in a suitable organic solvent, such as toluene and treated with about 1.2 equivalents of diphenylphosphoryl azide. To this mixture is added 1,8-diazabicyclo[5.4.0]undec-7-ene and the reaction mixture is stirred for about 16 hours at room temperature. The product is then isolated by standard extraction techniques. For example, the organic layer is separated and the aqueous layer is extracted with a suitable organic solvent, such as ethyl acetate. The organics are combined, dried over anhydrous magnesium sulfate, filtered and concentrated under vacuum to provide the azide (2).

In Scheme I, step B, the azido (2) is converted to the amine of formula II under standard conditions. For example, azido (2) is dissolved in a suitable organic solvent, such as tetrahydrofuran and a small amount of water. To this mixture is added about 1.1 equivalents of triphenylphosphine and the reaction mixture is stirred for about 16 hours. The reaction is then diluted with a suitable organic solvent, such as diethyl ether. The solution is rinsed with saturated sodium chloride, dried over anhydrous magnesium sulfate, filtered and concentrated under vacuum. The residue is then dissolved in a suitable organic solvent, such as ethyl acetate and ethyl acetate saturated with hydrogen chloride (excess) is added. The mixture is then concentrated under vacuum and the residue is dissolved in water. The aqueous phase is washed with diethyl ether and then ethyl acetate. The aqueous is then made basic with a suitable base, such as 5N sodium hydroxide and then extracted with a suitable organic solvent, such as methylene chloride. The organic extracts are combined, dried over anhydrous sodium sulfate, filtered and concentrated under vacuum to provide the amine of formula II.

In Scheme I, step C the amine of formula II is combined with the compound of formula III under conditions well known in the art to provide the compound of formula I. More specifically, for example, the amine of formula II is dissolved in a suitable organic solvent. Examples of suitable organic solvents include methylene chloride, tetrahydrofuran, and the like. The solution is treated with a slight excess of a suitable base, and then cooled to about --78° C. to about 0° C. Examples of suitable bases include triethylamine, pyridine, 1,8-diazabicyclo[5.4.0]undec-7-ene (DBU), and the like. To the stirring solution is added one equivalent of a compound of formula Ill. The term "Lg" as used herein refers to a suitable leaving group. Examples of suitable leaving groups include, Cl, Br, and the like. Cl is the preferred leaving group. The reaction mixture is stirred at about 0° C. to about 50° C. for about 0.5 hours to about 16 hours. The compound of formula I is then isolated and purified by techniques well known in the art, such as extraction techniques and chromatography. For example, the mixture is washed with 10% sodium bisulfate, the layers separated and the aqueous extracted with several times with a suitable organic solvent, such as methylene chloride. The organic extracts are combined, dried over anhydrous sodium sulfate, filtered and concentrated under vacuum. The residue is then purified by flash chromatography on silica gel with a suitable eluent such as ethyl acetate/hexane to provide the compound of formula I.

The compounds of formula I in which $R^1$ represents a 4-bromophenyl group may conveniently be converted into other compounds of formula I in which R represents another 4-substituted phenyl group by reaction with an appropriate boronic acid derivative, for example, a benzeneboronic acid derivative. The reaction is conveniently performed in the presence of a tetrakis (triarylphosphine)palladium(0) catalyst, such as tetrakis (triphenylphosphine)palladium(0) and a base such as potassium carbonate. Convenient solvents for the reaction include aromatic hydrocarbons, such as toluene. The temperature at which the reaction is conducted is conveniently in the range of from 0 to 150° C., preferably 75 to 120° C. Bis aromatic intermediates useful in the preparation of compounds of formula I may be prepared by reacting a bromoaromatic or bromoheteroaromatic compound with an aromatic or heteroaromatic boronic acid in an analogous manner.

More specifically, for example, to a degassed solution of a compound of formula I wherein $R^1$ represents a 4-bromophenyl group, approximately 1.5 equivalents of a benzeneboronic acid derivative, such as 3-fluorobenzeneboronic acid, and approximately 1.5 equivalents of potassium carbonate in a suitable organic solvent, such as toluene, is added a catalytic amount of bis(triphenylphosphine)palladium(II) dichloride. The mixture is heated to about 100° C. for about 16 hours, cooled to ambient temperature and diluted with ethyl acetate. The mixture is washed with water and the organic portion is separated. The aqueous portion is extracted with ethyl acetate and the combined organics are dried anhydrous magnesium sulfate, filtered and concentrated under vacuum. Chromatography on silica gel with a suitable eluent, such as ethyl acetate/toluene provides the desired bis aromatic compound of formula I.

The boronic acid derivative used as a starting material may be prepared by reacting a trialkyl borate, such as triisopropyl borate with an appropriate organolithium compound at reduced temperature. For example, 2-fluorobenzeneboronic acid may be prepared by reacting 2-fluorobromobenzene with butyllithium in tetrahydrofuran at about −78° C. to afford 2-fluorophenyl lithium, and then reacting this organolithium compound with triisopropyl borate.

Alternatively, the compounds of formula I in which $R^1$ represents a 4-bromophenyl group may be converted to a 4-(trimethylstannyl)phenyl or 4-(tri-n-butylstannyl)phenyl group by treatment of the corresponding bromide with a palladium(0) catalyst, such as tetrakis(triphenylphosphine)palladium(0) and hexaalkyldistannane, where the alkyl group is methyl or n-butyl, in an aprotic solvent such as toluene in the presence of a tertiary amine base such as triethylamine, at temperatures ranging from 80 to 140° C., preferably from 90 to 110° C.

The compounds of formula I in which $R^1$ represents a 4-(tri-n-butylstannyl)phenyl group may then be reacted with an aryl- or heteroarylbromide, such as 2-bromothiophene-5-carboxaldehyde, in the presence of a palladium(0) catalyst, such as tetrakis(triphenylphosphine)palladium(0), or a palladium(II) catalyst, such as bis(triphenylphosphine)palladium(II) dichloride, in an aprotic solvent, such as dioxane, at temperatures ranging from 80 to 140° C., preferably from 90 to 110° C., to afford the corresponding 4-(aryl)phenyl or 4-(heteroaryl)phenyl substituted compound.

The compounds of formula I in which $R^1$ represents a 4-bromophenyl group may be converted into other compounds of formula I in which $R^1$ represents a 4-substituted alkyl- or cycloalkylphenyl group, such as 4-cyclopentylphenyl by treatment of the corresponding bromide with an appropriate alkyl- or cycloalkyl Grignard reagent, such as cyclopentyl-magnesium bromide, in the presence of a palladium(li) catalyst, such as [1, 1'-bis(diphenylphosphino)ferrocene]-dichioropalladium(II) ($PdCl_2(dppf)$), in an aprotic solvent, such as diethyl ether at temperatures ranging from −78° C. to 25° C.

The compounds of formula I in which $R^1$ represents a 4-bromophenyl group may be converted into a 4-substituted carboxyaldehydephenyl(formylphenyl) group by reaction of the corresponding bromide with the carbon monoxide gas which is bubbled into the reaction under atmospheric pressure in the presence of a palladium(II) catalyst, such as bis(triphenyl-phosphine)palladium(II) dichloride and sodium formate in an aprotic solvent, such as dimethylformamide at temperatures ranging from 70 to 110° C., preferably at 90° C.

The compounds of formula I in which $R^1$ represents a 4-hydroxyphenyl group may be converted into other compounds of formula I in which $R^1$ represents an alkoxy group by treatment of the corresponding hydroxyphenyl group with an appropriate alkylhalide such as benzylbromide in the presence of sodium hydride in an aprotic solvent such as dimethylformamide at temperatures ranging from 25 to 100° C., preferably from 50 to 90° C.

The ability of compounds of formula I to potentiate glutamate receptor-mediated response may be determined using fluorescent calcium indicator dyes (Molecular Probes, Eugene, Oreg., Fluo-3) and by measuring glutamate-evoked efflux of calcium into GluR4 transfected HEK293 cells, as described in more detail below.

In one test, 96 well plates containing confluent monolayers of HEK cells stably expressing human GluR4B (obtained as described in European Patent Application Publication Number EP-A1-583917) are prepared. The tissue culture medium in the wells is then discarded, and the wells are each washed once with 200 µl of buffer (glucose, 10 mM, sodium chloride, 138 mM, magnesium chloride, 1 mM, potassium chloride, 5 mM, calcium chloride, 5 mM, N-[2-hydroxyethyl]-piperazine-N-[2-ethanesulfonic acid], 10 mM, to pH 7.1 to 7.3). The plates are then incubated for 60 minutes in the dark with 20 µM Fluo3-AM dye (obtained from Molecular Probes Inc., Eugene, Oreg.) in buffer in each well. After the incubation, each well is washed once with 100 µl buffer, 200 µl of buffer is added and the plates are incubated for 30 minutes.

Solutions for use in the test are also prepared as follows. 30 µM, 10 µM, 3 µM and 1 µM dilutions of test compound are prepared using buffer from a 10 mM solution of test compound in DMSO. 100 µM cyclothiazide solution is prepared by adding 3 µl of 100 mM cyclothiazide to 3 ml of buffer. Control buffer solution is prepared by adding 1.5 µl DMSO to 498.5 µl of buffer.

Each test is then performed as follows. 200 µl of control buffer in each well is discarded and replaced with 45 µl of control buffer solution. A baseline fluorescent measurement is taken using a FLUOROSKAN II fluorimeter (Obtained from Labsystems, Needham Heights, Mass. USA, a Division of Life Sciences International Plc). The buffer is then removed and replaced with 45 µl of buffer and 45 µl of test compound in buffer in appropriate wells. A second fluorescent reading is taken after 5 minutes incubation. 15 µl of 400 µM glutamate solution is then added to each well (final glutamate concentration 100 µM), and a third reading is taken. The activities of test compounds and cyclothiazide solutions are determined by subtracting the second from the third reading (fluorescence due to addition of glutamate in the presence or absence of test compound or cyclothiazide) and are expressed relative to enhance fluorescence produced by 100 µM cyclothiazide.

In another test, HEK293 cells stably expressing human GluR4 (obtained as described in European Patent Application Publication No. EP-A1-0583917) are used in the electro-physiological characterization of AMPA receptor potentiators. The extracellular recording solution contains (in mM): 140 NaCl, 5 KCl, 10 HEPES, 1 MgCl2, 2 CaCl2, 10 glucose, pH=7.4 with NaOH, 295 mOsm kg-1. The intracellular recording solution contains (in mM): 140 CsCl, 1 MgCl2, 10 HEPES, (N-[2-hydroxyethyl]piperazine-N1-[2-ethanesulfonic acid]) 10 EGTA (ethylene-bis (oxyethylene-nitrilo)tetraacetic acid), pH=7.2 with CsOH, 295 mOsm kg-1 With these solutions, recording pipettes have a resistance of 2–3 MΩ. Using the whole-cell voltage clamp technique (Hamill et al.(1981)Pflügers Arch., 391: 85–100), cells are voltage-clamped at −60mV and control current responses to 1 mM glutamate are evoked. Responses to 1 mM glutamate are then determined in the presence of test compound. Compounds are deemed active in this test if, at a test concentration of 10 µM, they produce a greater than 30% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an EC50 value, indicative of the potency of the test compound. Reversibility of test compound activity is determined by assessing control glutamate 1 mM responses. Once the control responses to the glutamate challenge are re-established, the potentiation of these responses by 100 µM cyclothiazide is determined by its inclusion in both the bathing solution and the glutamate-containing solution. In this manner, the efficacy of the test compound relative to that of cyclothiazide can be determined.

According to another aspect, the present invention provides a pharmaceutical composition, which comprises a compound of formula I or a pharmaceutically acceptable salt thereof as defined hereinabove and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1
Hard gelatin capsules are prepared
using the following ingredients:

| | Quantity (mg/capsule) |
|---|---|
| Active Ingredient | 250 |
| Starch, dried | 200 |
| Magnesium Stearate | 10 |
| Total | 460 |

The above ingredients are mixed and filled into hard gelatin capsules in 460 mg quantities.

Formulation 2
Tablets each containing 60 mg of
active ingredient are made as follows:

| | Quantity (mg/tablet) |
|---|---|
| Active Ingredient | 60 |
| Starch | 45 |
| Microcrystalline Cellulose | 35 |
| Polyvinylpyrrolidone | 4 |
| Sodium Carboxymethyl Starch | 4.5 |
| Magnesium Stearate | 0.5 |
| Talc | 1 |
| Total | 150 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

As used herein the term "patient" refers to a mammal, such as a mouse, guinea pig, rat, dog or human. It is understood that the preferred patient is a human.

As used herein the term "effective amount" refers to the amount or dose of the compound which provides the desired effect in the patient under diagnosis or treatment.

The particular dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

The following examples and preparations represent typical syntheses of the compounds of formula I as described generally above. These examples are illustrative only and are not intended to limit the invention in any way. The reagents and starting materials are readily available to one of ordinary skill in the art. As used herein, the following terms have the meanings indicated: "eq" refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "min" refers to minutes; "h" refers to hours; "° C." refers to degrees Celsius; "TLC" refers to thin layer chromatography; "HPLC" refers to high performance liquid chromatography; "$R_f$" refers to retention factor; "$R_t$" refers to retention time; "$\delta$" refers to part per million down-field from tetramethylsilane; "THF" refers to tetrahydrofuran; "DMF" refers to N,N-dimethylformamide; "DMSO" refers to methyl sulfoxide; "LDA" refers to lithium diisopropylamide; "EtOAc" refers to ethyl acetate; "aq" refers to aqueous; "iPrOAc" refers to isopropyl acetate; and "RT" refers to room temperature.

PREPARATION 3

2-Fluorobenzeneboronic Acid

A solution of 50 g (285.6 mmol) of 2-fluorobromobenzene in 400 mL of 15 tetrahydrofuran was cooled to −78° C. and 200 mL (320.0 mmol) of 1.6M n-Butyllithium was added via a cannula. The mixture was stirred at −78° C. for 60 minutes, then 98.9 mL (428.4 mmol) of triisopropyl borate was added via a cannula and stirring was continued for 60 minutes. The cooling bath was removed and the mixture was stirred at ambient temperature for 1.5 hours, then 150 mL of 6N hydrochloric acid was added and stirring was continued for 1.5 hours. To the mixture was added 100 mL of brine, and then the organic layer was separated and the aqueous layer was extracted three times with 30 mL each of ether. The combined organic extracts were dried (MgSO4), filtered and concentrated in vacuo. The residue was recrystallized from water to afford 25.2 g (63%) of the title compound.

PREPARATION 41

2-(4-bromophenyl)-N-(t-butoxycarbonyl)
ethylamine

To a room temperature solution of 10.0 g (50.0 mmol) of 4-bromophenethylamine and 11.0 g (50.0 mmol) of di-tert-butyl dicarbonate in 100 mL of chloroform was added 100 mL of saturated aqueous sodium bicarbonate. The mixture was stirred at room temperature for 1.5 hours and diluted with 100 mL of water. The organic layer was separated and the aqueous layer was extracted two times with 100 mL each of chloroform. The combined organics were washed once with 100 mL of 10% aqueous sodium bisulfate, dried (NaSO$_4$), filtered and concentrated in vacuo to afford 14.6 9 (97%). Mass Spectrum: M+1=301.

PREPARATION 42

4-cyanophenylboronic Acid

A solution of 10.0 g (54.9 mmol) of 4-bromobenzonitrile in 100 mL of tetrahydrofuran was cooled to −85° C. whereupon 36.0 mL (57.6 mmol) of 1.6 M solution of n-butyllithium in hexane was added. The mixture was stirred for five minutes and 19.0 mL (82.4 mmol) of triisopropylborate was added. The mixture was stirred at −85° C. for 30 minutes then warmed to ambient temperature over one hour.

To the mixture was added 35 mL of 5 N hydrochloric acid and stirring was continued for 2.5 hours. The mixture was diluted with 100 mL of saturated aqueous sodium chloride and extracted three times with 100 mL each of ethyl ether. The combined organics were dried (MgSO$_4$), filtered and concentrated in vacuo. The residue was recrystallized from water and filtered to afford 2.0 g (25%) of the title compound.

PREPARATION 45

Dibromoformaldoxime

A solution of 150 g (1.6 mole) of glyoxylic acid and 142 g (2.0 mole)of hydroxylamine hydrochloride in 1200 mL of water was stirred for 2 days. To the mixture was added slowly 342 g (4.1 mole) of sodium bicarbonate and 1000 mL of dichloromethane. The mixture was cooled to 0° C. and a solution of 147 mL (2.8 mole) bromine in 700 mL of dichloromethane was added dropwise. The mixture was stirred at ambient temperature for 18 hr. The organic layer was separated and the aqueous layer was extracted three times with 300 mL each of dichloromethane. The combined organic extracts were dried (MgSO$_4$), filtered and concentrated in vacuo to afforded 93.1 9 (28%) of the title compound.

PREPARATION 46

2-trimethylstannylthiazole

A. To a −78° C. solution of 5.0 g (58.7 mmol) of thiazole in 120 mL of tetrahydrofuran was added of 36.7 mL (58.7 mmol) of a 1.6 M solution of n-butyllithium in hexane. The mixture was stirred for 20 minutes whereupon 11.7 g (58.7 mmol) in 15 mL of tetrahydrofuran was added dropwise over 15 minutes. The cooling bath was removed and the mixture was stirred for two hours. The mixture was diluted with 100 mL of water and extracted three times with 100 mL ethyl ether. The combined organics were dried (MgSO$_4$), filtered and concentrated in vacuo. The residue was dissolved in 50 mL of ethyl ether, filtered through silica gel and concentrated in vacuo to afford 3.6 g (24%) of the title compound.

PREPARATION 49

4-(4-Bromophenyl)-1,1-dioxotetrahydro-1,2-thiazine

A. Ethyl 4-bromophenylacetate: A solution of 25.0 g (116.3 mmol) of 4-bromophenylacetic acid, 24.1 g (174.4 mmol) of potassium carbonate and 10.2 mL (127.9 mmol) of iodoethane in 250 mL of acetonitrile was heated at 70° C. for 16 hours. The mixture was cooled to ambient temperature, diluted with 200 mL of ethyl acetate and washed once with 200 mL of saturated aqueous sodium bicarbonate. The organic layer was separated and the aqueous layer was extracted three times with 75 mL each of ethyl acetate. The combined organics were dried (MgSO$_4$), filtered and concentrated in vacuo to afford 16.2 g (57%) of the title compound.

B. Phenyl 3-carbethoxy-3-(4-bromophenyl)propylsulfonate: A solution of 16.2 9 (66.6 mmol) of material from Step A, 4.6 g (33.3 mmol) of potassium carbonate and 4.4 g (16.7 mmol) of 18-crown-6 in 130 mL of toluene was heated to 90° C. and 6.1 g (33.3 mmol) of phenyl vinylsulfonate in 35 mL of toluene was added dropwise over one hour. The mixture was heated for 16 hours, cooled to ambient temperature and diluted with 100 mL of ethyl acetate. The mixture was washed once with 100 mL of half saturated brine. The organic layer was separated and the aqueous layer was extracted once with 50 mL of ethyl acetate. The combined organics were dried (MgSO$_4$), filtered and concentrated in vacuo. Chromatography (Waters 2000, 15% ethyl acetate/hexane) of the residue affords 4.8 g (17%) of the title compound.

Analysis calculated for $C_{18}H_{19}O_5SBr$: %C, 50.59; %H, 4.48. Found: %C, 50.61; %H, 4.47. Mass Spectrum: M+1= 428.

C. Phenyl 3-carboxy-3-(4-bromophenyl)propylsulfonate: To a solution of 4.8 g (11.3 mmol) of material from Step B in 40 mL of methanol was added 6.8 mL of 2 N aqueous sodium hydroxide. The mixture was stirred at ambient temperature for 5 hours and concentrated in vacuo. The residue was dissolved in 50 mL of water and extracted three times with 20 mL each of ethyl ether. The aqueous layer is acidified to pH 2 with 10% aqueous sodium bisulfate and extracted four times with 20 mL each of ethyl acetate. The combined ethyl acetate layers were dried (MgSO$_4$), filtered and concentrated in vacuo to afford 4.1 g (91%) of the title compound.

Analysis calculated for $C_{16}H_{15}O_5SBr$: %C, 48.13; %H, 3.79. Found: %C, 48.17; %H, 3.53.

Mass Spectrum: M =399.

D. Phenyl 3-carboxamido-3-(4-bromophenyl)propylsulfonate: To a 0° C. solution of 4.1 g (10.2 mmol) of material from Step C and 2.0 mL (14.3 mmol) of triethylamine in 23 mL of tetrahydrofuran was added 1.9 mL (14.3 mmol) of isobutyl chloroformate. The mixture was stirred at 0° C. for 25 minutes whereupon 11.2 mL (22.4 mmol) of a 2 N solution of ammonia in methanol was added. The cooling bath was removed and the mixture stirred for 16 hours. The mixture was diluted with 50 mL of ethyl acetate and washed once with 50 mL of water. The organic layer was separated and the aqueous layer was extracted three times with 25 mL each of ethyl acetate. The combined organics were dried (MgSO$_4$), filtered and concentrated in vacuo. Chromatography (250 g silica gel, 35% acetone/hexane) of the residue affords 1.7 g (44%) of the title compound.

Mass Spectrum: M=398.

E. 4-(4-Bromophenyl)-1,1,3-trioxotetrahydro-1,2-thiazine: To a 0° C. solution of 9.0 mL (9.0 mmol) of a 1.0 M tetrahydrofuran solution of potassium tert-butoxide in 15 mL of tetrahydrofuran was added a solution of 1.7 g (4.5 mmol) of material from Step D in 14 mL of tetrahydrofuran dropwise over 30 minutes. After stirring at 0° C. for two hours, the cooling bath was removed and stirring continued for 30 minutes. The mixture was diluted with 25 mL of water and extracted two times with 10 mL each of ethyl ether. The aqueous portion was acidified to pH 2 with 10% aqueous sodium bisulfate and extracted four times with 20 mL each of ethyl acetate. The combined ethyl acetate layers were dried (MgSO$_4$), filtered and concentrated in vacuo. Chromatography (75 g silica gel, 0.25% acetic acid/40% acetone/hexane) of the residue affords 0.2 g (17%) of the title compound.

Analysis calculated for $C_{10}H_{10}NO_3SBr$: %C, 39.49; %H, 3.31; %N, 4.61. Found: %C, 39.74; %H, 3.23; %N, 4.42.

Mass Spectrum: M =304.

F. To a suspension of 0.13 g (0.4 mmol) of material from Step E and 0.2 g (4.9 mmol) of sodium borohydride in 3 mL of dioxane was added 0.4 mL (4.9 mmol) of trifluoroacetic acid slowly via syringe. After stirring at ambient temperature for 30 minutes the mixture was heated to reflux for 5 hours. The mixture was cooled to ambient temperature, diluted with 3 mL of methanol and stirred for 16 hours. The mixture was removed and stirring continued for 30 minutes. The mixture was concentrated in vacuo, dissolved in 10 mL of ethyl acetate and washed two times with 5 mL each of 1 N hydrochloric acid and once with 5 mL of 20% saturated aqueous sodium bicarbonate/brine. The organics were dried ($MgSO_4$), filtered and concentrated in vacuo to afford 0.1 g (89%) of the title compound.

Analysis calculated for $C_{10}H_{12}NO_3SBr$: %C, 41.39; %H, 4.17; %N, 4.83. Found: %C, 41.10; %H, 4.34; %N, 4.76.

Mass Spectrum: M −1=289.

PREPARATION 51

N-(t-butoxycarbonyl)4-tributylstannylaniline

A. N-(t-Butoxycarbonyl)-4-bromoaniline: To a solution of 6.0 g (39.4 mmol) of 4-bromoaniline in 30 mL of tetrahydrofuran was added 69.8 mL (69.8 mmol) of a 1.0 M solution of sodium bis(trimethylsilyl)amide in tetrahydrofuran. To the mixture was added 7.6 g (34.9 mmol) of di-t-butyldicarbonate in 10 mL of tetrahydrofuran. The mixture was stirred at ambient temperature for one hour and concentrated in vacuo. The residue was dissolved in 50 mL of ethyl acetate and washed once with 50 mL of 10% aqueous sodium bisulfate. The organic layer was separated and the aqueous layer was extracted two times with 25 mL each of ethyl acetate. The combined organics were dried ($MgSO_4$), filtered and concentrated in vacuo. Chromatography (250 g of silica gel, 10% ethyl acetate/hexane) of the residue afforded 5.0 g (53%) of the title compound.

Analysis calculated for $C_{11}H_{14}NO_2Br$: %C, 48.55; %H, 5.19; %N, 5.15. Found: %C, 48.81; %H, 5.29; %N, 4.95.

Mass Spectrum: M −1=271.

B. A degassed solution of 4.9 g (18.0 mmol) of material from Step A, 2.6 mL (18.9 mmol) of triethylamine, 9.6 mL (18.9 mmol) of bis(tributyltin) and 1.0 g (0.9 mmol) of tetrakis(triphenylphosphine)palladium(0) in 45 mL of toluene was heated to 100° C. for 5 hours. The mixture was cooled to ambient temperature and diluted with 40 mL of ethyl acetate. The mixture was washed once with 50 mL of 10% aqueous sodium bisulfate, the organics separated and the aqueous layer extracted three times with 20 mL each of ethyl acetate. The combined organics were dried ($MgSO_4$), filtered and concentrated in vacuo.

Chromatography (400 g of silica gel, 5% ethyl acetate/hexane) of the residue afforded 1.4 g (16%) of the title compound.

Mass Spectrum: M+1=483.

PREPARATION 74

3-Tributyltin-2-cyclopenten-1-one

A −20° C. solution of hexabutylditin (4.6 g, 7.9 mmol) in dry THF (15 ml) was treated with nBuLi (4.9 ml, 7.9 mmol, 1.6 M solution in hexanes). The reaction mixture was stirred at −20° C. for 30 minutes and then cooled to −78° C. The mixture was treated with 3-ethoxy-2-cyclopenten-1-one (1.09g, 7.9 mmol) and the reaction mixture stirred at −78° C. for 30 minutes. A saturated, aqueous solution of ammonium chloride (2 ml) followed by water (30 ml) and the organic extracted with hexanes (2×30 ml). The combined organic layers were washed with brine (20 ml), dried over magnesium sulfate and concentrated in vacuo. This gave 2.7 g (93%) of the crude product which was used without further purification. NMR was consistent with the title structure.

PREPARATION 75

2-(4-(tri-n-butylstannyl)phenyl)ethyl methanesulfonamide

A. 2-(4-bromophenyl)ethyl methanesulfonamide: To a 0° C. solution of 10 g (50.0 mmol) of 4-bromophenethylamine and 5.6 g (55.0 mmol) of triethylamine in 150 mL of dichloromethane was slowly added a solution of 6.3 g (55.0 mmol) of methanesulfonyl chloride in 20 mL of dichloromethane. The mixture was allowed to warm to room temperature over two hours. The mixture was washed one time with 100 ml of 10% aqueous sodium bisulfate. The organic portion was separated and the aqueous portion was extracted three times with 50 mL each of dichloromethane. The combined organics were dried ($Na_2SO_4$), filtered and concentrated in vacuo to afford 14.0 g (100%) of the title compound.

B. To a solution of 14.0 g (50.0 mmol) of material from Part A above, 34.8 g (60.0 mmol) of bis(tributyltin) and 5.1 g (50.0 mmol) of triethylamine in 150 mL of toluene was added 2.9 g (2.5 mmol) of tetrakis(triphenylphosphine) palladium(0). The mixture was heated to 100° C. for 16 hours, cooled to room temperature and diluted with 100 mL of ethyl acetate. The mixture was washed one time with 100 mL of 10% aqueous sodium bisulfate. The organic portion was separated and the aqueous portion was extracted three times with 50 mL each of ethyl acetate. The combined organics were dried ($MgSO_4$), filtered and concentrated in vacuo. Chromatography (Waters Prep 2000, 5% ethyl acetate/hexane) afforded 10.0 g (40%) of the title compound.

Example 1

Preparation of N-(4-(3-thienyl)-1-phenethyl)2-propanesulfonamide

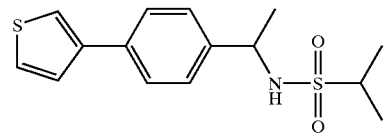

Scheme I, step A: 2-Azido-2-(4-bromophenyl)ethane: To a solution of 10.0 g (49.7 mmol) of 4-bromo-a-methylbenzyl alcohol and 16.4 g (59.6 mmol) of diphenylphosphoryl azide in 70 mL of toluene was added 9.1 g of 1,8-diazabicyclo [5.4.0]undec-7-ene and the mixture was stirred at room temperature for 16 hours. The reaction mixture was washed once with 30 mL of 10% aqueous sodium bisulfate. The organic layer was separated and the aqueous layer was extracted three times with 10 mL each of ethyl acetate. The combined organics were dried ($MgSO_4$), filtered and concentrated in vacuo to afford 11.2 g (100%) of the title compound.

Scheme I, step B: 2-(4-bromophenyl)ethylamine: To a solution of 11.2 g (49.7 mmol) of material from step A in 170 mL of tetrahydrofuran and 3.6 mL of water was added 14.3 g (54.7 mmol) of triphenylphosphine and the mixture was stirred for 16 hours. 100 mL of diethyl ether was added and the mixture was washed once with 100 mL of saturated aqueous sodium chloride. The organic portion was dried ($MgSO_4$), filtered and concentrated in vacuo. The residue was dissolved in 100 mL of ethyl acetate, 100 mL of hydrogen chloride saturated ethyl acetate was added and the mixture was concentrated in vacuo. Dissolve residue in 150 mL of water and extract once with 150 mL of diethyl ether and two times with 50 mL each of ethyl acetate. The aqueous portion was made basic with 5 N sodium hydroxide and extracted three times with 100 mL each of dichloromethane. The combined dichloromethane extracts were dried ($Na_2SO_4$), filtered and concentrated in vacuo to afford 7.8 g (78%) of the title compound.

Scheme I, step C: N-(1-(4-bromophenyl)ethyl)2-propanesulfonamide: To a 0° C. solution of 7.8 g (38.7 mmol) of material from step B and 6.5 g 42.6 mmol) of 1,8-diazabicyclo[5.4.0]undec-7-ene in 100 mL of dichloromethane was added 6.1 g (42.6 mmol) of isopropylsulfonyl chloride and the mixture was stirred and warmed to room temperature over 16 hours. The mixture was washed once with 75 ml of 10% aqueous sodium bisulfate, the organics were separated and the aqueous portion was extracted two times with 50 mL each of dichloromethane. The combined organic portions were dried ($Na_2SO_4$), filtered and concentrated in vacuo. Chromatography (500 g of silica gel, 20% ethyl acetate/hexane) of the residue afforded 5.1 g (43%) of the title compound.

Analysis calculated for $C_{11}H_{16}NO_2SBr$: %C, 43.15; %H, 5.27; %N, 4.57. Found: %C, 43.34; %H, 5.11; %N, 4.58.

Electrospray Mass Spectrum: M−2=304.

D. To a solution of 0.5 g (1.6 mmol) of N-(1-(4-bromophenyl)ethyl) 2-propanesulfonamide (prepared in step C above), 0.3 g (2.5 mmol) of thiophene-3-boronic acid and 0.3 9 (2.6 mmol) of potassium carbonate in 15 mL of 3:1 dioxane/water was added 0.1 9 (0.1 mmol) of tetrakis(triphenylphosphine)palladium. The mixture was heated to reflux for 16 hours, cooled and diluted with 10 mL of water. The mixture was extracted three times with 10 mL each of ethyl acetate. The combined organics were dried ($MgSO_4$), filtered and concentrated in vacuo. Chromatography (25 9 of silica gel, 20% ethyl acetate/hexane) of the residue gave a yellow solid which was recrystalized from chlorobutane to afford 0.2 g (40%) of the title compound.

Analysis calculated for $C_{15}H_{19}NO_2S_2$: %C, 43.15; %H, 5.27; %N, 4.57. Found: %C, 43.34; %H, 5.11; %N, 4.58.

Electrospray Mass Spectrum: M−1=308.

Example 2

Preparation of N-1-(4-(4-(2-methanesulfonamido ethyl)phenyl)phenyl) ethyl 2-propanesulfonamide

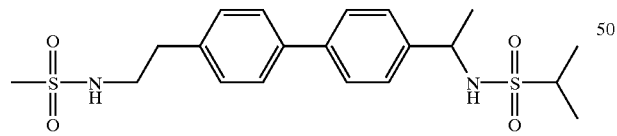

To a solution of 0.3 g (1.0 mmol) of N-(1-(4-bromophenyl)ethyl) 2-propanesulfonamide (prepared in Example 1, step C), 0.5 9 (1.0 mmol) of 2-(4-(tri-n-butylstannyl)phenyl)ethyl methanesulfonamide (obtained in preparation 75) in 3 mL of toluene was added 0.01 9 (0.05 mmol) of palladium acetate and 0.03 g (0.1 mmol) of triphenylphosphine. The mixture was heated to 100° C. for 16 hours. To this mixture was added 0.025 g (0.02 mmol) of tetrakis(triphenylphosphine)palladium and heating continued for 5 hours. Chromatography (25 g of silica gel, 50% ethyl acetate/hexane) of the of the cooled mixture afforded 0.01 g (2%) of the title compound.

We claim:
1. A method of potentiating glutamate receptor function in a mammal requiring such treatment, which comprises administering an effective amount of a compound of the formula:

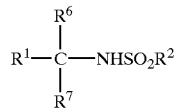

wherein $R^1$ represents a naphthyl group or a phenyl, furyl, thienyl or pyridyl group which is unsubstituted or substituted by one or two substituents selected independently from halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo(3–8C)cycloalkyl; halo (1–10C)alkyl; $(CH_2)_yX^1R^9$ in which y is 0 or an integer of from 1 to 4, $X^1$ represents O, S, $NR^{10}$, CO, COO, OCO, $CONR^{11}$, $NR^{12}CO$, $NR^{12}COCOO$ or $OCONR^{13}$, $R^9$ represents hydrogen, (1–10C)alkyl, (3–10C) alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; pyridyl; pyridazinyl; pyrimidinyl; dihydro-thienyl; dihydrofuryl; dihydmthiopyranyl; dihydropyranyl; dihydrothiazolyl; (1–4C) alkoxycarbonyldihydrothiazolyl; (1–4C) alkoxycarbonyldimethyldihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$ or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen, nitro, cyano, hydroxyimino, (1–10C) alkyl, (2–10C)alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, halo(1–10C)alkyl, (1–4C)alkoxycarbonyl(1–4C)alkyl, (1–4C) alkylsulfonylamino(1–4C)alkyl, (N(1–4C) alkoxycarbonyl) (1–4C)alkylsulfonylamino-(1–4C) alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group;

$R^2$ represents (1–6C)alkyl, (3–6C)cycloalkyl, fluoro (1–6C)alkyl, chloro(1–6C)alkyl, (2–6C)alkenyl, or (1–4C)alkoxy(1–4C)alkyl, or a group of formula $R^3R^4N$ in which $R^3$ and $R^4$ each independently represents (1–4C)alkyl or, together with the nitrogen atom to which they are attached form an azetidinyl, pyrrolidinyl, piperidinyl, morpholino, piperazinyl, hexahydroazepinyl or octahydroazocinyl group;

$R^6$ represents methyl; and $R^7$ represents hydrogen; or a pharmaceutically acceptable salt thereof.

2. A method of treating a cognitive disorder; a neurodegenerative disorder; age-related dementia; age-induced memory impairment; movement disorder; reversal of a drug-induced state; depression; attention deficit disorder; attention deficit hyperactivity disorder; psychosis; cognitive deficits associated with psychosis, or drug-induced psychosis in a patient, which comprises administering to a patient in need thereof an effective amount of a compound of the formula:

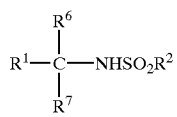

wherein $R^1$ represents a naphthyl group or a phenyl), furyl, thienyl or pyridyl group which is unsubstituted or substituted by one or two substituents selected independently from halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo(3–8C)cycloalkyl; halo (1–10C)alkyl; $(CH_2)_yX^1R^9$ in which y is 0 or an integer of from 1 to 4, $X^1$ represents O, S, $NR^{10}$, CO, COO, OCO, $CONR^{11}$, $NR^{12}CO$, $NR^{12}COCOO$ or $OCONR^{13}$, $R^9$ represents hydrogen, (1–10C)alkyl), (3–10C) alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^11$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl (1–4C) alkylpiperazinyl; thienyl; furyl; oxazolyl; isoxazolyl; pyrazolyl; imidazolyl: thiazolyl; pyridyl; pyridazinyl; pyrimidinyl; dihydro-thienyl; dihydrofuryl; dihydrothiopyranyl; dihydropyranyl; dihydrothiazolyl; (1–4C) alkoxycarbonyldihydrothiazolyl; (1–4C) alkoxycarbonyldimethyldihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents, a bond, O, NH, S, SO, $SO_2$, CO, CH(OH), CONH, NHCO, NHCONH, NHCOO, COCONH, $OCH_2CONH$ or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen, nitro, cyano, hydroxyimino, (1–10C) alkyl, (2–10C)alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, halo(1–10C)alkyl, (1–4C)alkoxycarbonyl(1–4C)alkyl, (1–4C) alkylsulfonylamino(1–4C)alkyl, (N-(1–4C) alkoxycarbonyl) (1–4C)alkylsulfonylamino-(1–4C) alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group;

$R^2$ represents (1–6C)alkyl, (3–6)cycloalkyl, fluoro(1–6C) alkyl, chloro(1–6C)alkyl, (2–6C)alkenyl; or (1–6C) alkoxy(1–4C)alkyl, or a group of formula $R^3R^4N$ in which $R^3$ and $R^4$ each independently represents (1–4C) alkyl or, together with the nitrogen atom to which they are attached form an azetidinyl, pyrrolidinyl, piperidinyl, morpholino, piperazinyl, hexahydroazepinyl or octahydroazocinyl group;

$R^6$ represents methyl; and $R^7$ represents hydrogen, or a pharmaceutically acceptable salt thereof.

3. A method for improving memory or learning ability in a patient, which comprises administering to a patient in need thereof an effective amount of a compound of the formula:

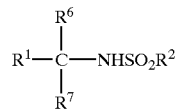

wherein $R^1$ represents a naphthyl group or a phenyl, furyl, thienyl or pyridyl group which is unsubstituted or substituted by one or two substituents selected independently from halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo(3–8C)cycloalkyl; halo (1–10C)alkyl; $(CH_2)_yX^1R^9$ in which y is 0 or an integer of from 1 to 4, $X^1$ represents O, S, $NR^{10}$, CO, COO), OCO, $CONR^{11}$, $NR_{12}CO$, $NR^{12}COCCOO$ or $OCONR^{13}$, $R^9$ represents hydrogen, (1–10C)alkyl, (3–10C)alkenyl, (3–1C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl (1–4C)alkylpiperazinyl; thienyl; furyl; oxazolyl; isoxazolyl; pyrazolyl; imidazolyl; thiazolyl; pyridyl; pyridazinyl; pyrimidinyl; dihydro-thienyl; dihydrofuryl; dihydrothiopyranyl; dihydropyranyl; dihydrothiazolyl; (1–4C) alkoxycarbonyldihydrothiazolyl; (1–4C) alkoxycarbonyldimethydihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, OCH$_2$CONH or CH=CH, L$^a$ and L$^b$ each represent (1–4C)alkylene, one of n and m is 0 or 1 and the other is 0, and R$^{14}$ represents a phenyl or heteroaromatic group which is unsubstituted or substituted by one or two of halogen, nitro, cyano, hydroxyimino, (1–10C) alkyl, (2–10C)alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and (CH$_2$)$_z$X$^3$R$^{15}$ in which z is 0 or an integer of from 1 to 4, X$^3$ represents O, S, NR$^{16}$, CO, CH(OH), COO, CONR$^{17}$, NR$^{18}$CO, NHSO$_2$, NHSO$_2$NR$^{17}$, NHCONH, OCONR$^{19}$ or NR$^{19}$COO, R$^{15}$ represents hydrogen, (1–10C)alkyl, phenyl(1–4C)alkyl, halo(1–10C)alkyl, (1–4C)alkoxycarbonyl(1–4C)alkyl, (1–4C)alkylsulfonylamino(1–4C)alkyl, (N-(1–4C)alkoxycarbonyl) (1–4C)alkylsulfonylamino-(1–4C)alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and R$^{16}$, R$^{17}$, R$^{18}$ and R$^{19}$ each independently represents hydrogen or (1–10C)alkyl, or R$^{15}$ and R$^{16}$, R$^{17}$, R$^{18}$ or R$^{19}$ together with the nitrogen atom to which they are attached form an azetidinyl, pyrrolidinyl, piperidinyl or morpholino group;

R$^2$ represents (1–6C)alkyl, (3–6C)cycloalkyl, fluoro(1–6C)alkyl, chloro(1–6C)alkyl, (2–6C)alkenyl, or (1–4C)alkoxy(1–4C)alkyl, or a group of formula R$^3$R$^4$N in which R$^3$ and R$^4$ each independently represents (1–4C)alkyl or, together with the nitrogen atom to which they are attached form an azetidinyl, pyrrolidinyl, piperidinyl, morpholino, piperazinyl, hexahydroazepinyl or octahydroazocinyl group;

R$^6$ represents methyl; and

R$^7$ represents hydrogen; or a pharmaceutically acceptable salt thereof.

* * * * *